United States Patent [19]
Davis

[11] 4,024,189
[45] May 17, 1977

[54] CHEMICAL PROCESS
[75] Inventor: Wayne T. Davis, Baton Rouge, La.
[73] Assignee: Ethyl Corporation, Richmond, Va.
[22] Filed: June 2, 1975
[21] Appl. No.: 582,628
[52] U.S. Cl. .......................................... 260/585 A
[51] Int. Cl.² ........................................ C07C 85/02
[58] Field of Search .............................. 260/585 A
[56] References Cited
UNITED STATES PATENTS 3,294,851  12/1966  Roobol et al. ............ 260/585 A X
3,471,562  10/1969  Wakeman et al. ......... 260/585 A X
3,542,876  11/1970  Blaney et al. ............. 260/585 A X
3,686,250   8/1972  Lanier ........................ 260/448 A Primary Examiner—Daniel E. Wyman
Assistant Examiner—John J. Doll
Attorney, Agent, or Firm—Donald L. Johnson; John F. Sieberth; Shelton B. McAnelly

[57] ABSTRACT

It is disclosed that alkyl amines are produced from a mixed olefin feed containing vinyl olefins with internal olefins or vinylidene olefins as impurities by a plural step process in which the mixed olefins are subjeced to a selective isomerization wherein vinylidene olefins are converted to branched internal olefins, the olefins are then hydrobrominated to produce bromoalkanes, the bromoalkanes are selectively dehydrohalogenated whereby the secondary bromoalkanes are converted to olefins leaving the primary bromoalkanes substantially unaffected, thé primary bromoalkanes being subjected to amination with ammonia or a primary or secondary amine whereby they are converted to amine hydrobromides. The amine hydrobromides are then converted to amines, and the amines are recovered.

17 Claims, 1 Drawing Figure

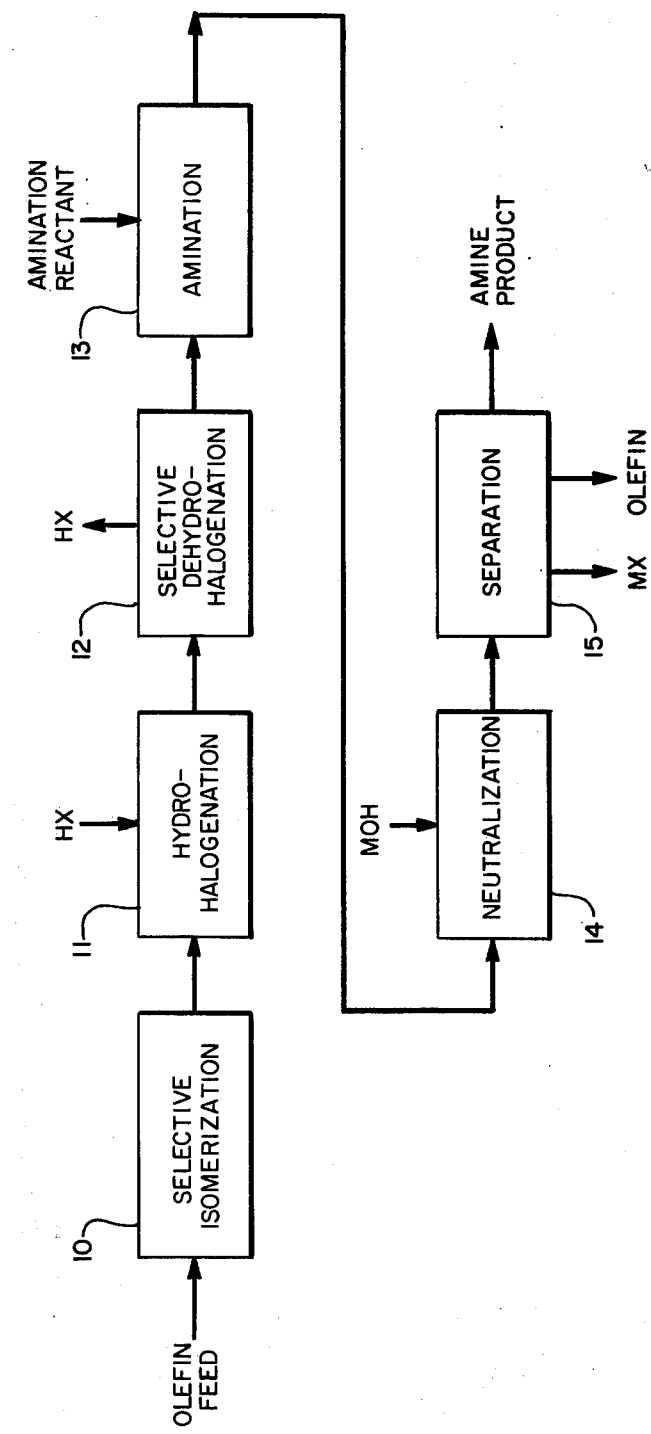

CHEMICAL PROCESS

BACKGROUND OF THE INVENTION

1. Field of the Invention

This invention relates to the preparation of primary, secondary or tertiary alkyl amines from olefins by a process involving the conversion of the olefins to alkyl halides and the amination of the alkyl halides by reaction with an amine having at least one replaceable hydrogen atom. Amine hydrohalides are thus produced which may be converted to amines by reaction with caustic.

2. Description of the Prior Art

The production of amines from olefins by processing including the conversion of the olefins to haloalkane and then reacting the haloalkane with an amine having a replaceable hydrogen atom is known in the prior art. Unfortunately, the prior art process is not suitable for the production of amines with a very high primary alkyl group content unless the starting olefins have a high vinyl purity because internal olefins and vinylidene olefins, common impurities, also undergo the conversions producing amines with branched chain alkyl groups or with the alkyl groups linked to the nitrogen atom via an internal carbon atom of the alkyl group.

As a result, the use of the foregoing process in the prior art has been limited to the use of more costly, less readily available olefins or to the preparation of less desired products of mixed carbon skeletal structures.

SUMMARY OF THE INVENTION

The present invention art the foregoing prior at problem and permits the production of the more desired amines with straight chain terminally linked hydrocarbon groups even when using starting olefins that contain, in addition to vinyl olefins, impurity olefins of either or both the vinylidene olefin and internal olefin types. As a result of using the present process, one can produce the highly desired product amines from readily available olefins.

In accordance with the present invention, a process is provided for preparing amines of the formula:

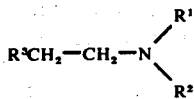

from olefins of the formula $R^3CH=CH_2$ in admixture with internal olefins $R^4CH=CHR^5$ wherein $R^1$, $R^2$ and $R^3$ are hydrogen or alkyl having from 1 to about 24 carbon atoms, and $R^4$ and $R^5$ are alkyl having from 1 to about 24 carbon atoms. In the process, the feed olefin mixture is hydrobrominated to produce bromoalkanes which are then selectively dehydrohalogenated whereby the 1-bromoalkanes are substantially unaffected while the secondary bromoalkanes are converted to olefins. Amination of the 1-bromoalkanes with an amine having at least one replaceable hydrogen atom converts the 1-bromoalkanes to amine hydrobromides. The amine hydrobromides thus obtained are converted into amines, typically by reaction with a base such as NaOH or KOH and the amines thus produced are recovered. Preferably the amine reacted with the bromoalkanes is ammonia or a mono- or di-lower alkyl amine having from 1 to about 6 carbon atoms per alkyl group.

In accordance with another aspect of the present invention, a process is provided for preparing amines of the formula:

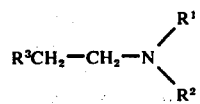

from olefins of the formula $R^3CH=CH_2$ in admixture with internal olefins or olefins of the formula

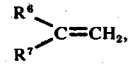

wherein $R^1$, $R^2$ and $R^3$ are hydrogen or alkyl having from 1 to about 24 carbon atoms, $R^6$ and $R^7$ being alkyl having from 1 to about 24 carbon atoms. In this process, the olefin mixture is subjected to a selective isomerization wherein

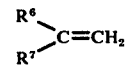

olefins are converted to internal olefins. The internal olefins, like the vinyl olefins, are then hydrobrominated to produce bromoalkanes. The bromoalkanes are then selectively dehydrohalogenated whereby 1-bromoalkanes are substantially unaffected while secondary bromoalkanes are converted to olefins, and the 1-bromoalkanes are subjected to amination with an amine having at least one replaceable hydrogen atom, the 1-bromoalkanes being converted to amine hydrobromides. Following this operation, the amine hydrobromides in the intermediate product are converted into amines, preferably by a neutralization reaction with a suitable base liberating a bromide salt of the base used in neutralization, and the amines thus produced are recovered from the salt.

Preferably the amine reacted with the 1-bromoalkane is ammonia or a mono- or di-lower alkyl mono amine having from 1 to about 6 carbon atoms per alkyl group. In a preferred aspect, the amine reacted with the 1-bromoalkane is monomethyl amine, monoethyl amine, mono-n-propyl amine, monoisopropyl amine, monoisobutyl amine or mono-n-butyl amine. Preferably, the amine reacted with the 1-bromoalkane is a short chain secondary amine such as dimethyl amine or diisopropyl amine, especially dimethyl amine and the product is a tertiary amine having one long chain alkyl group whose origin is the olefin and two short chain alkyl groups whose origin is the amine reactant fed to the amination reaction. Typical preferred tertiary amine products are lauryl dimethyl amine, tetradecyl dimethyl amine, hexadecyl dimethyl amine, lauryl di-isopropyl amine, tetradecyl di-isopropyl amine and hexadecyl di-isopropyl amine.

Preferably, the number of carbon atoms in $R^3$ as well as in $R^6$ plus $R^7$ is from about 6 to about 28, especially from about 8 to about 18, more preferably from about 10 to about 14, typically about 10, 12 or 14.

Preferably, the temperature of the selective isomerization step is from about 0° to about 100° C, especially from about 40° to about 60° C. Preferably, this step is conducted in the presence of a suitable catalyst such as aluminum-silicate. Preferably, the hydrobromination step is performed at a temperature of from about 0° to about 75° C, especially from about 10° to about 50° C and in the presence of a free radical catalyst to promote anti-Markownikoff addition of HBr to the olefin.

Preferably the temperature at the selective dehydrohalogenation step is from about 150° to about 300° C, especially from about 220° to about 250° C, and the pressure is from about ½ to about 10 atmospheres. Preferably, the reaction is performed in the presence of a suitable catalyst such as magnesium oxide.

Preferably the temperature at the amination step is from about 50° to about 200° C, especially from about 100° to about 150° C, and the pressure is from about 10 to about 100 atmospheres, especially from about 30 to about 60 atmospheres and the reaction is performed in the presence of a 1:1 to a 50:1 molar excess, especially at 10:1 to 15:1 molar excess of dialkyl amine.

The single FIGURE of the drawing shows a preferred embodiment of the features of the present invention wherein feed olefins are converted to amine.

DISCUSSION

The single FIGURE of the drawing shows in block form a preferred embodiment of the features of the present invention. In this process, vinyl olefins which may be contaminated with internal olefins or vinylidene olefins, or both, are subjected to a selective isomerization at 10, then hydrohalogenated at 11 with a hydrogen halide, especially HBr. The resulting bromoalkanes are selectively dehydrohalogenated at 12, the 1-bromoalkanes being retained as such to be aminated with a suitable aminating reactant, such as dimethyl amine, at 13. Resulting amine hydrobromides are neutralized at 14 with a suitable base and the product amines are recovered at 15.

The present processing is of considerable advantage in the preparation of amines because overall it in effect provides a way to selectively convert straight chain terminal olefins to predominantly straight chain alkyl groups which are linked via a terminal carbon atom thereof to the nitrogen atoms of the amine using, as starting olefins, olefin mixtures which can contain, in addition to vinyl olefins, vinylidene olefins or internal olefins or both. Such capability is particularly significant in view of the fact that excellent, low cost, vinyl olefins are readily available in large quantity produced by chain growth using processing such as that of U.S. Pat. No. 3,663,647 and that such olefins frequently contain up to about 10 percent each of vinylidene olefins and internal olefins. Since the removal of either vinylidene olefins or internal olefins from vinyl olefins is not an easy or inexpensive operation, the present process which does not require the prior removal of such impurites to avoid the formation of amine impurities containing branched alkyl groups or groups linked to the nitrogen via a secondary carbon atom provides a significant improvement.

Important features of the present invention are the performance of certain steps of the process in a selective manner whereby high purity straight chain 1-bromoalkanes are obtained to react with an aminating reactant having at least one replaceable hydrogen atom to form amine hydrobromides characterized by the presence of a straight chain terminally linked alkyl group. In such processing, the presence in the product amines of alkyl groups linked to the nitrogen via a carbon atom other than a terminal carbon atom of the alkyl group is avoided by using a selective dehydrobromination wherein the bromoalkanes in which the bromine atom is linked to a non-terminal carbon atom are dehydrohalogenated while those wherein the bromine atom is linked to a terminal carbon atom are not dehydrohalogenated. By virtue of this selective dehydrohalogenation operation, bromine atoms linked to non-terminal carbon atoms of the carbon skeleton are selectively split-off producing olefinic molecules which do not react with the aminating agent. The olefins resulting from dehydrohalogenation can be removed from the unaffected 1-bromoalkanes before or after the amination reaction. Since the olefins are more volatile than the 1-bromoalkanes or the amine product in most cases, distillation removal of the olefins is practical. If the percentage of internal olefins in the starting olefins is high or if the selectivity of hydrobromination to 1-bromoalkanes is not high, it may be preferred to remove the olefins from the 1-bromoalkanes prior to the amination reaction to avoid monopolizing amination reactor volume with undesired molecules. In some instances, the olefins may constitute a desirable diluent during the amination reaction and hence it may be desirable to retain them during the amination and remove them subsequently. Although such actors may influence the economics in different ways, the amine product of the present process is essentially the same with the foregoing methods of removal of the olefins.

The volume of olefins produced in the selective dehydrohalogenation step is influenced to a significant degree by the selectivity one attains in the formation of 1-bromoalkanes by the hydrobromination of the starting olefins. In general, olefins of the internal variety react with hydrogen bromide always forming non-terminal bromoalkanes, usually called secondary bromoalkanes, without significant capability for selectivity to produce primary-bromoalkanes. On the other hand, terminal olefins can be hydrobrominated to primary bromoalkanes with a high degree of selectivity using appropriate catalysts. Using free radical catalysts such as ozone, lauroyl peroxide, or benzoyl peroxide, in the hydrohalogenation of vinyl olefins, the bromine attaches to a terminal carbon atom with a high degree of selectivity, usually higher than 90 percent, frequently higher than 95 percent. Thus by an appropriate selection of conditions in the hydrohalogenation step one can vary the amount of olefins produced by the dehydrohalogenation; however, the formation of some olefins by dehydrohalogenation occurs with the process even when using starting olefins that are free of internal olefins.

The avoidance of formation of amine products having branched alkyl groups when the starting olefins contain vinylidene olefins requires a different approach because proximately branched 1-bromoalkanes that result from the hydrobromination of vinylidene olefins cannot be selectively removed from the straight chain 1-bromoalkanes by the dehydrohalogenation conversion to olefins. Accordingly, the avoidance of proximately branched terminally linked alkyl groups in the product amines is avoided by a selective isomerization of starting olefins prior to the hydrohalogenation. Such a selective isomerization of vinylidene olefins to trisubstituted internal olefins is described in U.S. Pat. No. 3,686,250. This selective operation does not adversely affect vinyl olefins and even has the beneficial result of converting some straight chain internal olefins into vinyl olefins. The trisubstituted olefins that are obtained from the vinylidene olefins behave very much as internal olefins in the hydrohalogenation, selective dehydrohalogenation and amination operations of the present process and hence evolve as olefins separable from 1-bromoalkanes or from product amines without excessive difficulty.

As a result of the operations performed in the present process, one obtains amines having a high percentage of straight chain terminally linked alkyl groups even when starting with vinyl olefins containing vinylidene and/or internal olefins as impurities.

In the performance of the present process, it is possible to combine the selective dehydrohalogenation and amination into a single operative step thereby producing the olefin containing amine hydrobromide intermediate compositions previously discussed from which amines free of olefins may be obtained readily. The present process may be used to produce a wide variety of primary, secondary or tertiary amines depending upon the olefinic reactant and the aminating reactant used. The process is particularly well suited to the preparation of alkyl dimethyl amines and alkyl diisopropyl amines useful as such or useful for conversion to amine oxides for use in detergent formulations. For such use, the alkyl groups preferably are long chain, have from about 12 to about 16 carbon atoms, have straight chain carbon skeleton structure and are linked to the nitrogen atom in the amine molecule via a terminal carbon atom. Such compounds are produced in the present process by using olefins having 12 to 16 carbon atoms per molecule and appropriate secondary amines such as dimethyl amine or diisopropyl amine as the aminating reactant.

Reaction conditions used for the various steps of the process are important to achieve the optimum desired selectivity at the various steps; however, based upon the present disclosure one of ordinary skill in the art is enabled to practice the invention optimizing the various steps to the extent desired without the need for further invention.

Typical olefinic reactants useful in the present invention include vinyl olefins such as propylene-1, butene-1, pentene-1, hexene-1, heptene-1, octene-1, nonene-1, decene-1, undecene-1, dodecene-1, tridecene-1, tetradecene-1, pentadecene-1, hexedecene-1, heptadecene-1, octadecene-1, nonadecene-1, eicosene-1, heneicosene-1, docosene-1, tricosene-1, tetracosene-1, pentacosene-1, hexacosene-1, and triacontene-1, and corresponding isomeric vinylidene and internal olefins, individually as well as in various combinations of two or more different molecular weights. Usual olefin mixture are isomers of the same molecular weights since the separation of isomeric olefins of the same molecular weight by simple processes such as distillation is difficult. Where the feed olefins contain remote branching, i.e., at carbon atoms which are not linked to the olefinic double bonds, they react in the present process and produce products analogous to the vinyl olefins. A typical branched, non-vinylidene, terminal olefin which can be used to produce amines containing remotely branched alkyl groups is 6-methyl undecene-1. Preferred olefins are unsubstituted or contain only compatible substitution such as alkyl groups and the like which do not undergo adverse or undesired side reactions in the process.

Typical amine reactants are those previously set forth herein especially the short chain secondary mono amines such as dimethyl amine, diisopropyl amine and the like. Corresponding primary amines as well as ammonia also are typical amine reactants. Other suitable amine reactants include amines having two or more nitrogen atoms per molecule. The formation of undesired products in the amination reaction is minimized by using a large excess of the aminating reactant, preferably from about 5:1 to about 25:1 mols of aminating agent per atom of bromine present in the alkyl bromide fed. A more preferred ratio is from about 10:1 to about 15:1. Preferably the amination is conducted in the presence of from about 0.1 to about 25 wt. percent of water calculated on the basis of the sum of the amine reactant fed and water.

The following examples indicate preferred embodiments and aspects of the present invention.

EXAMPLE I

A mixture of isomeric tetradecenes containing 97.2 wt. percent tetradecenes, 0.6 wt. percent decenes, 1.3 wt. percent dodecenes, 0.7 wt. percent hexadecenes and 0.2 wt. percent octadecenes, distributed 91.9 mol percent vinyl olefins, 3.7 mol percent vinylidene olefins and 4.4 mol percent internal olefins was passed through a packed tower catalyst bed in a 3/4 i.d. × 64 inch steel column at a 1hsv = 1 (about 500 milliliters per hour) and at about 95° C. The catalyst was an aluminum silicate similar to Grace 979.

The isomerized product was analyzed by VPC (Vapor Phase Chromatography). It was found that no vinylidene olefin content >CH=CH$_2$ remained; however, the branched internal olefins were 2.42 wt. percent and the linear olefins were 97.58 wt. percent. As explained in U.S. Pat. No. 3,686,250, the foregoing selective isomerization converts vinylidene olefins into branched internal olefins.

865 Grams of the foregoing isomerized olefin mixture was then subjected to a batch hydrobromination wherein the olefins were sparged with ozone in oxygen produced by a Welsbach Ozone Generator. To produce about 0.3 mol percent ozonide in the olefins.

The ozonized olefin was placed in a flask equipped with a magnetic stirrer and provision for chilled propanol cooling to 0°–5° C. HBr was then fed to the liquid in the flask for 4 hours to react substantially all the olefin. The resultant alkyl bromide was found by NMR to contain 79.6 mol percent 1-bromoalkane and 20.4 mol percent 2-bromoalkanes and higher order bromoalkanes.

The bromoalkane product from the hydrobromination step was then selectively dehydrobrominated to convert secondary alkyl bromides to olefin and HBr by heating 300 grams of the mixed alkyl bromides with 0.2308 grams anhydrous MgO at 230°–240° C while sparging with nitrogen to remove HBr evolved.

The mixture of olefin and bromoalkane was then subjected to distillation to remove the olefins. The composition of the distillation feed (by NMR) was 77.3 mol percent 1-bromoalkane; 19 mol percent internal olefin, 3.1 mol percent trisubstituted olefin, and 0.6 mol percent vinyl olefin. The olefin removed contained 20.8 mol percent 1-bromoalkane, 0.8 mol percent secondary bromoalkanes, 70.5 mol percent internal olefin, 5.1 mol percent tri-substituted olefin, 2.3 mol percent vinyl olefin and 0.6 mol percent vinylidene olefin. The bromoalkane remaining was 99.3 mol percent 1-bromoalkane, 0.3 mol percent internal olefin and 0.3 mol percent tri-substituted olefin.

Eighty-five grams of the resulting bromoalkane was then mixed with 26 grams of H$_2$O and charged to a 2-liter titanium Parr autoclave. The autoclave was then closed and purged with nitrogen. Then 234 grams of dimethylamine was charged to the autoclave. The reactor was heated to slightly above 100° C with agitation, cooled to 70° C and excess dimethylamine vented off. 18.35 Grams of NaOH in 55.0 grams H₂O was then added to the crude product, the mixture stirred for 15 minutes and allowed to stand for 30 minutes. The water and organic phases were then separated yielding 95 ml of product phase and 60 ml of aqueous phase. The product was then washed with 25 percent aqueous caustic and dried with NaOH pellets.

The purity of the product tertiary amine was 99.7–99.8 mol percent, the balance being olefin.

EXAMPLE II

Example I was repeated with the difference that the olefin was not removed from the bromoalkanes prior to the amination reaction but rather was allowed to remain with the bromoalkane through the amination and was removed from the product amine. Similar product amine was obtained. These examples indicate the preparation from olefins of alkyl dimethyl amines of the formula

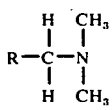

wherein R is substantially all straight chain alkyl even where the starting olefins contain some vinylidene olefins and some internal olefins, thereby permitting the use of low cost olefin feeds.

EXAMPLE III 34.7 pounds of a mixture of isomeric dodecenes and tetradecenes in approximately 2:1 weight ratio containing 92.8 mol percent vinyl olefins, 4.4 mol percent vinylidene olefins and 2.8 mol percent internal olefins plus small amounts of decenes, hexadecenes and octadecenes was sparged with ozone in oxygen produced by Welsbach Ozone Generator. The sparging was conducted with an ozone rate of 7 grams per hour over a period of 108 minutes to produce 0.3 mol percent ozonide in the olefins based on the theoretical stoichiometry.

1,500 cc of the ozonized olefin was added to the hydrobromination flask which was a 3 liter round bottom Morton three-neck flask fitted with a frit for adding HBr deep into the liquid and an addition funnel for adding olefin below the liquid level. System temperature was maintained by a constant temperature pump-around isopropanol bath. The system had a dip leg that could be immersed into the liquid for product withdrawal. The dip leg discharged near the bottom of a graduated cylinder filled with aqueous bicarbonate to scrub HBr from the product stream. Product was taken off the top of the scrubber.

A heel of 1,500 cc ozonized olefin was placed in the hydrobromination flask which was held at 0°–5° C. The dip leg was raised to prevent liquid removal. Initially, HBr was fed by adding it to the effluent stream of a Vanton Flex Pump which recirculated the flask contents through a cooler. This reaction was conducted for 4 hours to react all the olefin to form an alkyl bromide heel.

To the heel thus obtained, olefin was fed continuously at from 4.6 to 8 cc per minute at a reaction temperature of 0°–5° C and pressure of 4 psig until all the ozonized olefin had been fed, HBr being fed continuously through the frit.

The alkyl bromide product was removed from the reactor by lowering the dip leg into the liquid discharging the liquid into the scrubber. Where a second run was desired, a heel of about 1,500 cc of the product was retained in the flask for start-up of the next run without need for the preliminary hydrobromination.

Product taken from the scrubber was again washed with sodium bicarbonate solution and then extracted from the bicarbonate with petroleum ether. The mix was then heated to drive off the petroleum ether and the remaining product dried with anhydrous sodium carbonate.

The product analyzed by NMR (mol percent).

| | |
|---|---|
| α-bromoalkane | 93.4 |
| β-bromoalkane | 6.6 |
| | 100.0 |

Alkyl bromide from the foregoing procedure was aminated in a 13 gallon glass lined autoclave. In a typical amination, 16.37 pounds of the alkyl bromide (0.0595 mol) and 3.57 pounds of water (water = 10 percent of total charge of dimethyl amine plus water) were charged to the autoclave. Then 32.2 pounds of dimethyl amine was charged. The reactor was heated to 100° C, which temperature was held for 1 hour (160–200 psig). The reactor was cooled to 70° C and excess dimethyl amine vented off. The temperature was then lowered to 50° C. A solution of 25 percent caustic (0.0595 mol + 6 percent excess NaOH) was charged to the reactor and the system was then stirred for 30 minutes. The system was allowed to stand for about 15 minutes and the bottom layer decanted. The product was vacuum stripped of dimethyl amine and then the remaining product was flashed. The product was then distilled in a 2" packed vacuum distillation column to remove residual olefin.

The product amine and the olefin were analyzed by NMR (mol percent).

| | Olefin | | | | |
|---|---|---|---|---|---|
| | Vinyl | Internal | Trisubstituted | Vinylidene | Amine |
| Amine | 0 | 0.2 | 0.8 | 0.1 | 98.9 |
| Olefin | 85 | 4.5 | 0 | 10.4 | 0 |

By VPC analysis the amine product was 95 percent ("straight chain primary" C₁₂₋₁₄) dimethyl amine, 3.6 (non-"straight chain primary" C₁₂₋₁₄) dimethyl amine with 1.7 percent residual olefin.

I claim:

1. A process for preparing amines of the formula:

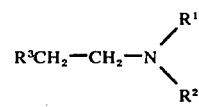

from olefins of the formula R³CH=CH₂ in admixture with internal olefins R⁴CH=CHR⁵ wherein R¹, R² and R³ are hydrogen or alkyl having from 1 to about 24 carbon atoms and $R^4$ and $R^5$ are alkyl having from 1 to about 24 carbon atoms, which comprises:
- A. hydrobrominating the feed olefin mixture to produce bromoalkanes,
- B. selectively dehydrohalogenating the bromoalkanes from A whereby 1-bromoalkanes are substantially unaffected and secondary bromoalkanes are converted to olefins,
- C. subjecting to amination with an amine having at least one replaceable hydrogen atom the 1-bromoalkanes from step B whereby the 1-bromoalkanes are converted to amine hydrobromides,
- D. converting amine hydrobromides in the product from C into amines and
- E. recovering the amines thus produced.

2. The process of claim 1 wherein the amine reacted at C is ammonia or mono- or di-lower alkyl amine having from 1 to about 6 carbon atoms per alkyl.

3. A process for preparing amines of the formula:

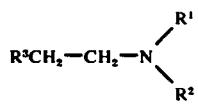

from olefins of the formula $R^3CH=CH_2$ in admixture with internal olefins or olefins of the formula

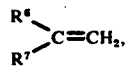

wherein $R^1$, $R^2$ and $R^3$ are hydrogen or alkyl having from 1 to about 24 carbon atoms, $R^6$ and $R^7$ being alkyl having from 1 to about 24 carbon atoms, which comprises:
- A. subjecting the olefin mixture to a selective isomerization wherein

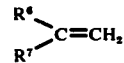

olefins are converted to internal olefins,
- B. hydrobrominating the olefin mixture from step A,
- C. selectively dehydrohalogenating the bromoalkanes from B whereby 1-bromoalkanes are substantially unaffected and secondary bromoalkanes are converted to olefins,
- D. subjecting to amination with an amine having at least one replaceable hydrogen atom the 1-bromoalkanes from step C whereby the 1-bromoalkanes are converted to amine hydrobromides,
- E. converting amine hydrobromides in the product from D into amines and
- F. recovering the amines thus produced.

4. The process of claim 3 wherein the amine reacted at the amination step is ammonia or mono- or di-lower alkyl amine having from 1 to about 6 carbon atoms per alkyl.

5. The process of claim 3 wherein the amine reacted at the amination step is monomethyl amine, monoethyl amine, mono-n-propyl amine, monoisopropyl amine, monoisobutyl amine or mono-n-butyl amine.

6. The process of claim 3 wherein the amine reacted at the amination step is dimethyl amine or diisopropyl amine.

7. The process of claim 3 wherein the amine reacted at the amination step is dimethyl amine.

8. The process of claim 3 wherein the number of carbon atoms in $R^3$ and in $R^6$ plus $R^7$ is from about 6 to about 28.

9. The process of claim 3 wherein the number of carbon atoms in $R^3$ as well as the sum of the carbon atoms in $R^6$ and $R^7$ is from about 8 to about 18.

10. The process of claim 3 wherein the number of carbon atoms in $R^3$ as well as the sum of the carbon atoms in $R^6$ and $R^7$ is from about 10 to about 14.

11. The process of claim 3 wherein the number of carbon atoms in $R^3$ as well as the sum of the carbon atoms in $R^6$ and $R^7$ is about 10.

12. The process of claim 3 wherein the temperature at the selective isomerization step is from about 40° to about 60° C.

13. A process in accordance with claim 3 wherein the hydrobromination step is performed at a temperature of from about 10° to about 50° C.

14. A process in accordance with claim 3 wherein the hydrobromination step in performed at a temperature of from about 10° to about 50° C and in the presence of a free radical catalyst to promote anti-Markownikoff addition of HBr to the olefin.

15. The process of claim 3 wherein the temperature at the selective dehydrohalogenation step is from about 220° to about 250° C, the pressure is from about ½ to about 10 atmospheres and the reaction is performed in the presence of magnesium oxide catalyst.

16. The process of claim 3 wherein the temperature at the amination step is from about 100° to about 150° C, the pressure is from about 30 to about 60 atmospheres and the reaction is performed in the presence of a 10:1 to 15:1 molar excess of dialkyl amine.

17. The process of claim 3 wherein at least a part of the olefins produced at the selective dehydrohalogenation step are removed from the 1-bromoalkanes prior to the amination step.

* * * * *

UNITED STATES PATENT OFFICE
CERTIFICATE OF CORRECTION

PATENT NO. : 4,024,189
DATED : MAY 17, 1977
INVENTOR(S) : WAYNE T. DAVIS

It is certified that error appears in the above-identified patent and that said Letters Patent are hereby corrected as shown below:

Item [54] reads "Chemical Process", should read -- Process for Preparing Amines --. Item [57], line 4, reads "subjeced", should read -- subjected --. Column 1, line 1, reads "Chemical Process", should read -- Process for Preparing Amines --; line 32, reads "invention art the foregoing prior at", should read -- invention avoids the foregoing prior art --. Column 4, line 24, reads "actors", should read -- factors --. Column 6, line 38, reads "Generator. To", should read -- Generator to --.
Column 9, line 30, reads

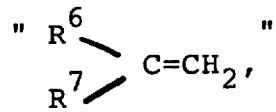

should read -- 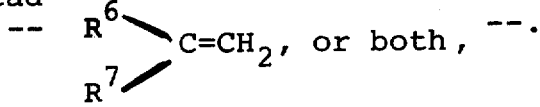

Column 10, line 36, reads "step in", should read -- step is --.

Signed and Sealed this twenty-third Day of August 1977

[SEAL]

Attest:

RUTH C. MASON
Attesting Officer

C. MARSHALL DANN
Commissioner of Patents and Trademarks